United States Patent [19]

Welker

[11] Patent Number: 4,841,785
[45] Date of Patent: Jun. 27, 1989

[54] VANISHING CHAMBER CONSTRUCTION FOR LIQUID SAMPLER

[75] Inventor: Brian Welker, Sugarland, Tex.

[73] Assignee: Welker Engineering Company, Sugarland, Tex.

[21] Appl. No.: 212,276

[22] Filed: Jun. 27, 1988

Related U.S. Application Data

[63] Continuation of Ser. No. 59,424, Jun. 8, 1987, abandoned.

[51] Int. Cl.⁴ ............................................. G01N 1/14
[52] U.S. Cl. ................................................ 73/863.84
[58] Field of Search ................ 73/864, 863.84, 863.83, 73/863.81, 864.35, 864.34

[56] References Cited

U.S. PATENT DOCUMENTS

| 4,403,518 | 9/1983 | Welker | 73/864.34 |
| 4,440,032 | 4/1984 | Welker | 73/863.84 |
| 4,562,749 | 1/1986 | Clark | 73/863.84 |

Primary Examiner—Stewart J. Levy
Assistant Examiner—Robert R. Raevis
Attorney, Agent, or Firm—Gunn, Lee & Miller

[57] ABSTRACT

In a vanishing chamber pump mechanism, an improved apparatus is set forth. The preferred embodiment incorporates a resilient plug adapted to work opposite an anvil which relatively reciprocates to pump sample trapped in the hemispherical chamber within said resilient plug. The improved version incorporates a metallic insert axially centered in the hemispherical cavity, and it is anchored in place by an enlarged root extending into the body which is intervally cast around the insert.

3 Claims, 1 Drawing Sheet

U.S. Patent  Jun. 27, 1989  4,841,785
FIG.1
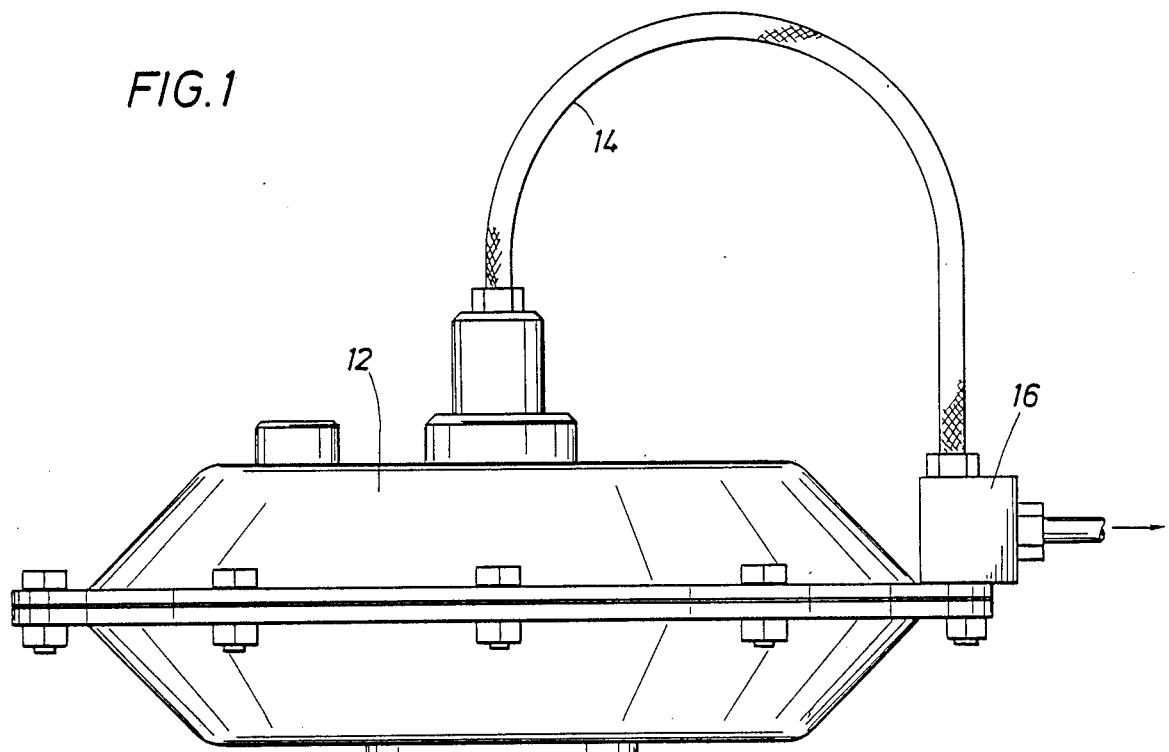
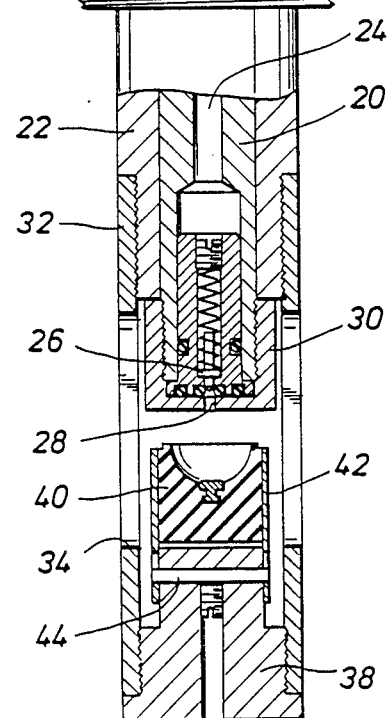
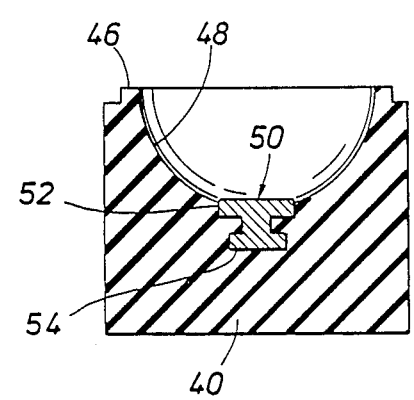
FIG.2

VANISHING CHAMBER CONSTRUCTION FOR LIQUID SAMPLER

This is a continuation of application Ser. No. 059,424 filed on June 8, 1987, now abandoned.

BACKGROUND OF THE DISCLOSURE

A liquid sampler set forth in this disclosure is a device for extracting a sample flow from a larger liquid stream. A typical circumstance of use is taking a sample from a crude oil source. The liquid sampler of this disclosure is a device which is provided by the Welker Engineering Company, the sampler being described by various patents including U.S. Pat. No. 4,403,518. The liquid sampler construction utilizes a reciprocating pump rod driven by some type of motor (a diaphragm motor in the preferred embodiment). The lower of the metal rod is normally described as an anvil which works opposite a collection head. The collection head has a cylindrical rubber plug within a surrounding metal sleeve. It is positioned so that the anvil moves relatively against the rubber plug. The rubber plug has a dished region surrounded by a peripheral lip. This lip makes sealing contact and thereby captures fluid within the dished region. As pressure is applied against the rubber plug, the volume of the dished region becomes smaller and disappears. Liquid in that region is forced out of the chamber and flows through a small opening in the anvil. It flows past a spring loaded poppet valve and into a passage for removal for a subsequent use.

The described apparatus has met with great success. It is able to collect minute samples in routine operation with a great variety of liquids and subject to pressure over a wide range. The device has indefinite life in practically all regards except that the resilient plug is subject to failure through resilient fatigue. Interesting, the failure mode is first observed in the resilient plug by the formation of stress cracks or fractures at the center of the dished region. The dished region is more or less in the shape of a hemisphere to provide the chamber which collects the liquid which is subsequently forced out through the poppet valve connected at a small opening in the anvil. The failure normally occurs approximately at the center of the chamber, this being the volume opposite a small opening in the anvil which evacuates liquid flow. Liquid flows from that region into the poppet valve under pressure as the chamber in the resilient plug disappears. The failure is thus immediately adjacent to the small opening which communicates with the poppet valve. It may begin with relatively small stress fractures in the resilient plug but they soon extend and result in catastrophic failure of the resilient plug. The plug then must be replaced.

Replacement is not so difficult but it is difficult to predict when the resilient plug might fail. Thus, the pump device must be inspected periodically to determine whether or not the resilient plug has begun to fail. Since failure is not precisely predictable, periodic servicing of the liquid sampler must be undertaken at no small expense. This is particularly true when the liquid sampler is located at remote or unmanned locations, as for instance in the gathering lines connecting several oil wells with a storage tank battery. It is not uncommon to install this type of device at a tank battery to obtain liquid samples. The samples are necessary so that the collected crude can be periodically tested as a sample. This relates significantly to the value of the crude as well as the specific assay for purposes of post production treatment. While there are many reasons to install such device, it is equally important to assure that it continues to operate successfully without failure. In particular, it is important to assure that the liquid sampler continues to collect samples without failure of the resilient member.

With the foregoing in mind, the present disclosure is directed to an improved resilient plug cooperative with a liquid sampler system. The resilient plug is cylindrical on the exterior and has a top end surrounding peripheral face for contact with the anvil. The plug is centrally dished and has an approximately hemispherical cavity. It is integrally cast about a small metal insert located at the center line of the cylindrical body and therefore at a center line axis through the chamber. The insert is a small disc having a narrow neck and an enlarged root which is surrounded by the cast resilient material to ensure anchoring. It is sufficiently large in diameter to confront the opposite opening in the anvil. This prevents dimpling of the resilient material by extruding into the opening. This thereby prevents stress fractures from building up in the center portion of the resilient plug and markedly changes the life of the device.

While the foregoing sets forth the present invention in summary form, many other objects and advantages will be observed on a review of the detailed description of the present apparatus found below.

In the Drawings

So that the manner in which the above recited features, advantages and objects of the present invention are attained and can be understood in detail, more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

FIG. 1 is a side view of a liquid sampler having an anvil opposite a resilient plug in accordance with the teachings of the present disclosure for capturing liquid removed by the liquid sampler; and FIG. 2 is an enlarged detailed view of the resilient plug of the present disclosure showing details of construction and including a central metal member as will be described.

DETAILED DESCRIPTION OF PREFERRED EMBODIMENT

In the drawings, the numeral 10 identifies a liquid sampler. This liquid sampler is constructed with a diaphragm motor within the housing 12. It has an outlet line 14 which connects with a suitable fitting 16, and the line can then be extended to some kind of sample collection container such as a removable sample bottle. The diaphragm motor includes a central protruding threaded sleeve 18 which is typically threaded through the wall of a pipe line or into some kind of liquid container. The apparatus below the thread extends into the interior of the liquid container to extract sample quantities. Moreover, it is adapt to be extended into a storage tank, pipeline or other oil or liquid containiing structure. Further, the threads are typically standard threads such as NPT or other alternate threaded connections.

Below the threaded connection, and extending somewhat in the fashion of a wand, an elongate body encloses a reciprocating rod 20, the body being formed of a surrounding sleeve 22. An axial passage 24 extends along the reciprocating rod. The diaphragm motor provides pumping motion to the rod 20. The passage 24 delivers collected sample through the outlet line 14 for subsequent removal. The passage 24 is closed by a spring loaded poppet valve 26. The poppet valve is immediately adjacent to an opening 28 centered in an anvil 30. Liquid is delivered through the opening 28 past the poppet valve element and then into the passage. As will be understood, every stroke forces a minuet quantity of liquid past the poppet valve.

The anvil 30 has the form of a metal cap or crown over the lower end of the reciprocating rod 20. Appropriate O-ring seals are included on the interior to prevent leakage around the edges. Moreover, the anvil is exposed to the liquid to be sampled. To this end, the surrounding external sleeve 22 threads to a continuation sleeve 32 which has a port or window 34. Ideally, two or more windows are included to assure that the liquid to be sampled is in the region of the chamber to be described.

The sleeve 32 threads to a base member 38 which in turn supports the resilient plug 40. The plug 40 is surrounded on the outer cylindrical face by a metal shield 42. This provides structural confinement to the resilient plug so that it does not flow and thereby distort from the cylindrical shape. Moreover, the shield 42 is held in position by a pin 44. This permits the shield to reciprocate slightly in response to the relative shortening of the resilient plug 40.

Going now to FIG. 2 of the drawings, the resilient plug 40 is shown in greater detail. It has an upper peripheral lip 46 which surrounds a central hemispherical chamber 48. On the central axis of the cylindrical plug and circular hemisphere chamber 48, a metallic insert 50 is located. It has an enlarged head 52 and an enlarged root 54, the two being joined together by a narrow neck. The root 54 serves as an anchor to fasten the metallic insert 50 in place. It is preferably placed in the mold at the time of the fabrication of the resilient plug 40. In rough estimation, the head 52 is approximately 15 to 20 percent of the diameter of the hemisphere 48. Also, it must be larger in diameter than the opening 28 which works opposite the resilient plug. Further, the root 54 must be sufficiently deep into the body of the plug that it is able to hold and secure the location of the metal insert 50. On the other hand, the root need not extend much deeper than this. The resilient plug 40 is made of a material in the range of hardness to about 70 to 90 durometer on the Shore A scale. It is preferably made of materials which are not subject to chemical attack by the liquid being sampled such as various synthetic rubber compounds including butadiene. The plug does not dimple because the metal insert does not extrude into the opening. This protects the plug from extruding into a dimple in the opening. This in turn prevents stress build up around the insert and enables the plug to last much longer. The resilient plug is protected from premature stress failure.

While the foregoing is directed to the preferred embodiment, the scope thereof is determined by the claims which follow.

What is Claimed:

1. In a vanishing chamber liquid sampling system having a motor relatively moving a resilient plug against an anvil which anvil seals against the resilient plug and the resilient plug has a chamber for receiving a fluid to be sampled, the improvement which comprises a non-yielding insert in the resilient plug exposing a solid face at a spherical surface defining said fluid receiving chamber and located opposite an opening through the anvil for evacuating liquid from the chamber.

2. The plug of claim 1 wherein said insert has a metal head sufficiently large to cover over and block the opening opposite said resilient plug and further including a root on said insert for anchoring said insert in the body of said resilient plug.

3. The plug of claim 1 wherein said plug is circular and said resilient plug spherical chamber surface is a hemispherical chamber surface centered on the longitudinal axis of said circular plug which is formed as a cylinder, and further including means positioning said insert and a root on said insert within the body of the resilient plug to anchor said insert fixedly in said resilient plug.

* * * * *